United States Patent [19]

Pater

[11] Patent Number: 5,081,198

[45] Date of Patent: Jan. 14, 1992

[54] TOUGH, HIGH PERFORMANCE, ADDITION-TYPE THERMOPLASTIC POLYMERS

[75] Inventor: Ruth H. Pater, Tabb, Va.

[73] Assignee: The United States of America as represented by the Administrator of the National Aeronautics and Space Administration, Washington, D.C.

[21] Appl. No.: 434,195

[22] Filed: Nov. 13, 1989

Related U.S. Application Data

[63] Continuation-in-part of Ser. No. 250,480, Sep. 28, 1988, abandoned.

[51] Int. Cl.⁵ .............................................. C08F 26/06
[52] U.S. Cl. .................................... 526/262; 526/248; 526/249; 525/275; 525/421; 525/422; 525/426
[58] Field of Search ....................... 526/262, 248, 259; 525/275, 421, 422, 426

[56] References Cited

U.S. PATENT DOCUMENTS 4,365,034 12/1982 Grimes et al. ..................... 524/256
4,451,402 5/1984 D'Alelis et al. .................... 526/262

FOREIGN PATENT DOCUMENTS

WO9001522 2/1990 PCT Int'l Appl. ................ 525/422

Primary Examiner—Joseph L. Schofer
Assistant Examiner—Alex H. Walker
Attorney, Agent, or Firm—George F. Helfrich

[57] ABSTRACT

A tough, high performance polyimide is provided by reacting a triple bond conjugated with an aromatic ring in a bisethynyl compound with the active double bond in a compound containing a double bond activated toward the formation of a Diels-Adler type adduct, especially a bismaleimide, a biscitraconimide, or a benzoquinone, or mixtures thereof. Addition curing of this product produces a highly linear polymeric structure and heat treating the highly linear polymeric structure produces a thermally-stable aromatic addition-type thermoplastic polyimide, which finds utility in the preparation of molding compounds, adhesive compositions, and polymer matrix composites.

16 Claims, 4 Drawing Sheets

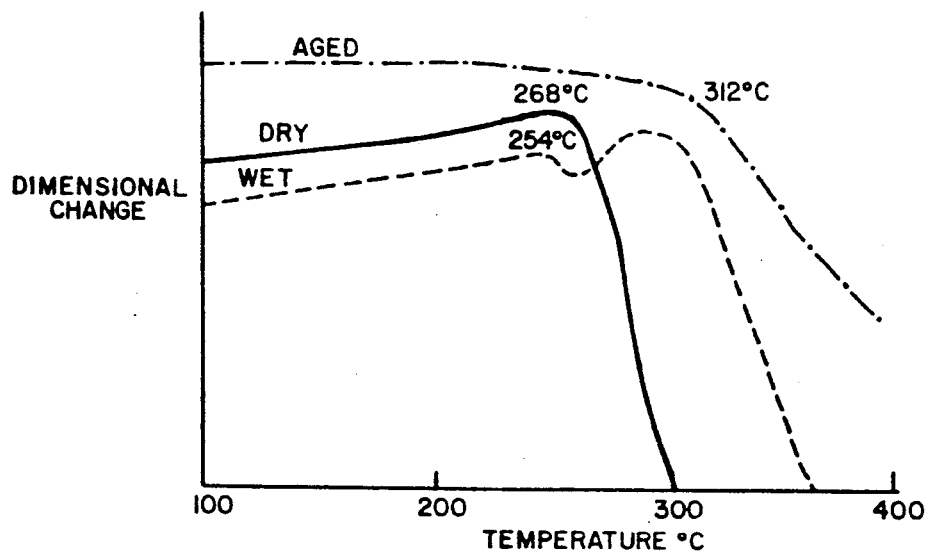
FIGURE 5
FIGURE 6
Dendritic pattern ← Fracture propagation
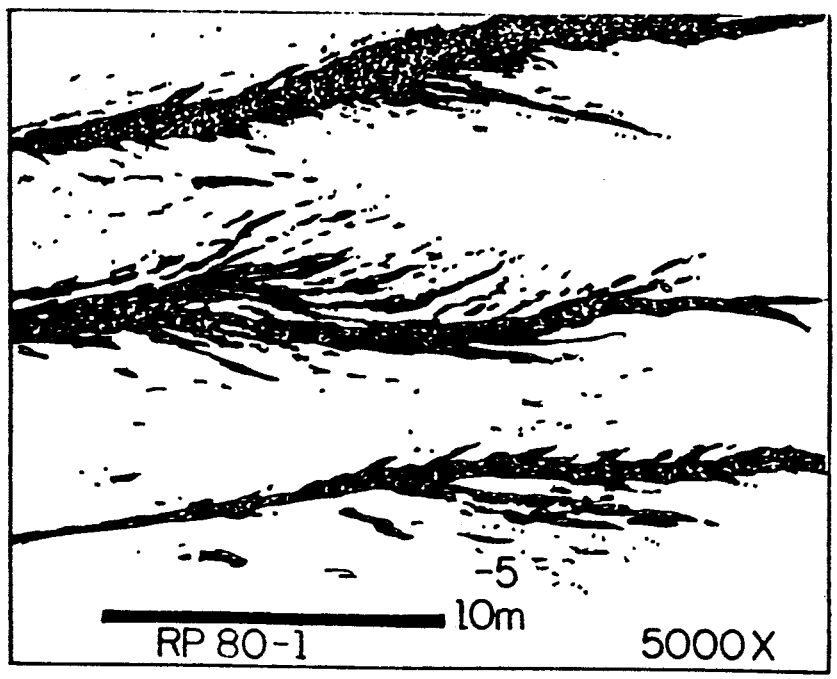

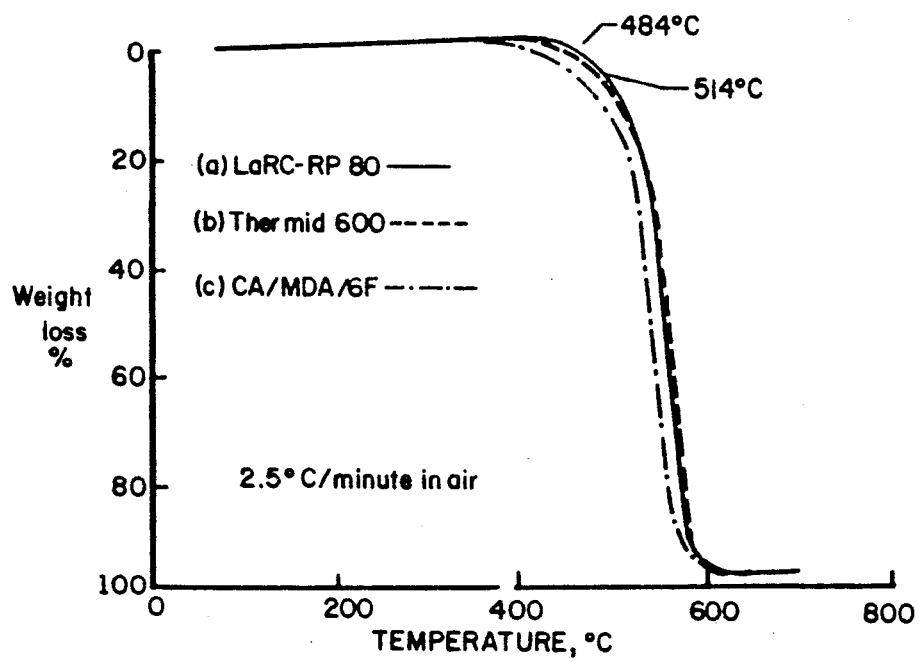
FIGURE 7
FIGURE 8
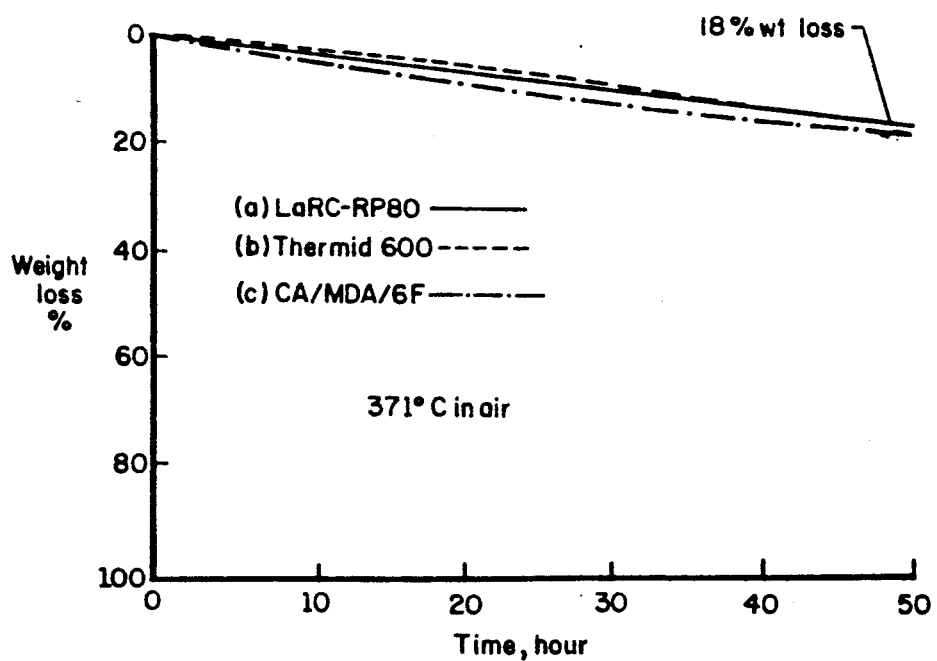

TOUGH, HIGH PERFORMANCE, ADDITION-TYPE THERMOPLASTIC POLYMERS

ORIGIN OF THE INVENTION

The invention described herein was made by an employee of the U.S. Government and may be manufactured and used by or for the Government for governmental purposes without the payment of any royalties thereon or therefor.

CROSS REFERENCE

This application is a continuation-in-part of application Ser. No. 07/250,480, filed Sept. 28, 1988 now abandoned.

BACKGROUND OF THE INVENTION

1. Field of the Invention

The present invention relates generally to tough, high performance, thermoplastic polymers. It relates particularly to addition-type thermoplastic polymers, which are polymers having an addition curing which leads to a linear structure.

2. Description of Related Art

High performance thermosetting and thermoplastic polyimides are under extensive experimental and developmental evaluation for a large number of aerospace structural applications because of their high glass transition temperatures ($T_g$s), excellent mechanical performance, and ability to withstand harsh environments, such as heat, moisture and chemicals. However, the poor processability and lack of damage tolerance remain the fundamental problems of these materials which seriously inhibit their widespread use in fabricating large aerospace structures. Thermosetting polyimides are, in general, easy-to-process but inherently brittle, whereas thermoplastic polyimides are tough but difficult-to-process. What is needed is a polymer that can be processed like a thermoset while possessing the toughness of a thermoplastic.

An addition-type thermoplastic (hereafter referred to as "ATT") polymer has characteristics of such an ideal polymer. An ATT is defined as a polymer that has an addition curing which leads to a linear structure. Such a polymer is non-classical in that it has similarities to two major classical categories: thermosets (addition curing with a crosslinked structure) and thermoplastics (condensation reaction cured having a linear structure). Because of their addition curing and linear structure, ATT polymers can have toughness (like thermoplastics) and can be easily processed (like thermosets).

Arnold et al (U.S. Pat. No. 4,675,370) and Kirchhoff (U.S. Pat. No. 4,540,763) and others have developed a synthetic route for making ATT polymers. Their synthesis involves the Diels-Alder reaction of a benzocyclobutene and a bismaleimide, as illustrated by the following reaction.

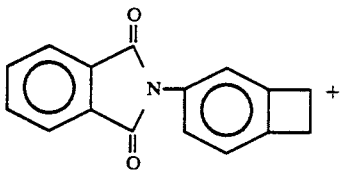

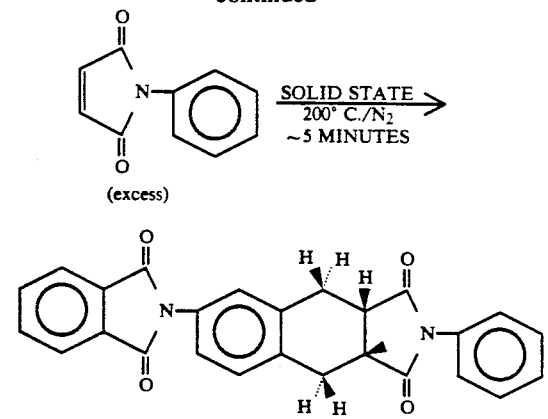

The scope of this synthetic reaction is limited by the availability of benzocyclobutene compounds and other factors, such as processing, properties and cost effectiveness of the end use products.

Similarly, D'Alelio (U.S. Pat. No. 4,451,402) has also used the Diels-Alder reaction between a conjugated diyne and a bismaleimide to obtain ATT polymers. This reaction is shown below:

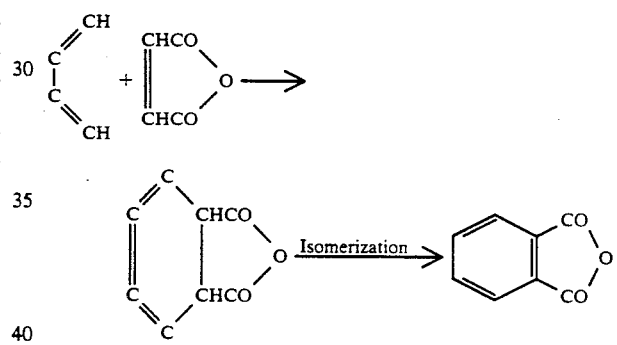

Further, Grimes et al (U.S. Pat. No. 4,365,034) have developed a methodology to improve the processability of the acetylene-terminated Thermid polyimide system.

However, none of these prior art products exhibit the desired combination of properties provided by the present invention.

Accordingly, the primary object of this invention is to provide a synthetic reaction which forms stable aromatic rings in the backbone of an ATT polymer, thereby combining high temperature performance and thermo-oxidative stability with toughness and easy processibility, and minimizing or eliminating the necessity for property tradeoffs often observed in conventional polymer synthesis.

Another object of this invention is to obtain polymers having the combination of easy processability, toughness, high temperature performance and good thermo-oxidative stability in one material.

Yet another object is to develop methods for making and using these polymers.

It is another object of the present invention to provide novel monomeric materials for use in attaining the primary object above.

SUMMARY OF THE INVENTION

According to the present invention, the foregoing and additional objects are attained by reacting a triple bond conjugated with an aromatic ring in a bisethynyl compound with the active double bond in a compound containing a double bond activated toward the formation of a Diels-Alder type adduct.

The general reaction scheme is illustrated below:

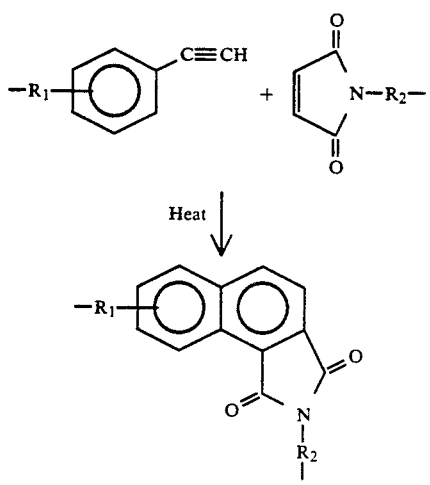

Especially good results have been obtained if the second reactant is one of or a mixture of a bismaleimide, a biscitraconimide, and a benzoquinone. A highly linear polymer structure is produced if the reaction product is addition cured; and a thermally-stable aromatic addition-type thermoplastic polyimide is produced by heat treating this highly linear polymeric structure. The bisethynyl compound and the compound containing a double bond activated toward the formation of a Diels-Alder type adduct are reacted in stoichiometric quantities, as well as in off-stoichiometric quantities, especially in a mole ratio range between about 7:1 and 1:7. The tough, high performance polyimides according to the present invention find special utility in the preparation of molding compounds, adhesive compositions, and polymer matrix composites. Novel monomeric materials used in the preparation of the polyimides according to the present invention have the following general structural formula:

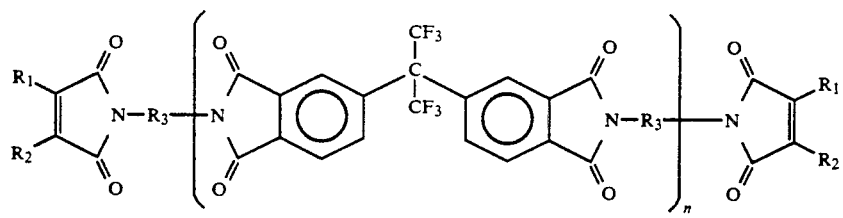

wherein $R_1$ and $R_2$ are hydrogen or alkyl and $R_3$ is an alkyl or aryl radical.

BRIEF DESCRIPTION OF THE DRAWINGS

For a more complete understanding of the present invention, including its objects and attending benefits, reference should be made to the Detailed Description of the Preferred Embodiments, which is set forth below. This Description should be read together with the accompanying drawings, wherein:

FIG. 5 shows the results of thermomechanical analyses of (a) the polyimide product of FIG. 2 in the dry state; (b) the polyimide product of FIG. 2 in the wet state; and (c) the polyimide product of FIG. 2 which has been aged for six hours at 371° C. in air;

FIG. 6 is a scanning electron micrograph of the polyimide product of FIG. 2;

FIG. 7 shows the results of thermogravimetric analyses of (a) the polyimide product of FIG. 2; (b) the commercially available starting material of FIG. 2; and (c) the novel monomeric material of FIG. 2; and FIG. 8 shows the results of isothermal (371° C.) thermogravimetric analyses of (a) the polyimide product of FIG. 2; (b) the commercially available starting material of FIG. 2; and (c) the novel monomeric material of FIG. 2.

DESCRIPTION OF THE PREFERRED EMBODIMENTS

Figure 1:
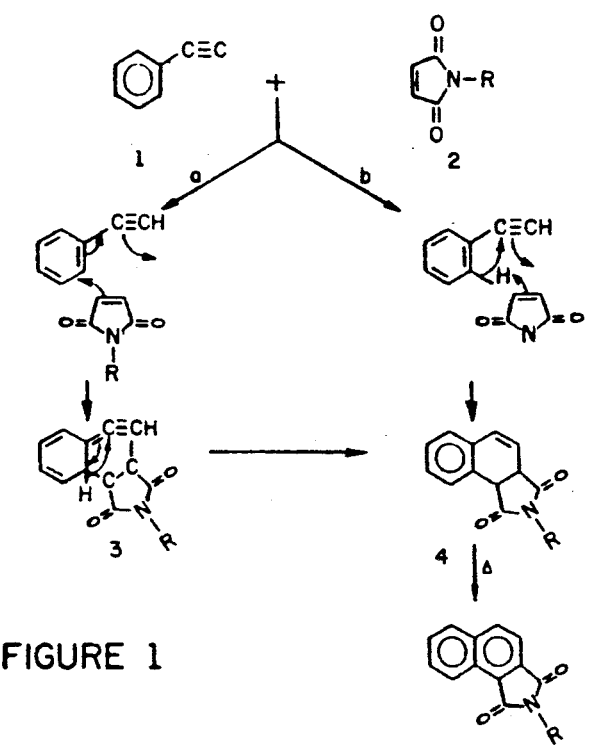
FIG. 1 is a reaction equation showing possible mechanisms for the synthesis of addition-type thermoplastic polymers.

The concept of the ATT synthesis is schematically depicted in FIG. 1. The synthesis may proceed through the cycloaddition of an acetylene-terminated prepolymer with a compound containing a double bond activated toward the formation of a Diels-Alder type adduct, such as a bismaleimide, a biscitraconimide, or a benzoquinone. The reaction sites are the triple bond conjugated with an aromatic ring in a bisethynyl compound and the active double bond in a compound containing a double bond activated toward the formation of a Diels-Alder type adduct. The cycloaddition may proceed via at least two reaction pathways as shown in (a) and (b) of FIG. 1. Both involve a concerted process. Pathway (a) forms a highly strained intermediate (3) containing an allene functionality from the Diels-Alder reaction of the $4\pi$ electrons in the conjugated triple bond with the $2\pi$ electrons in the maleimide double bond. To release the ring strain, compound (3) would most likely quickly rearrange itself to give the more stable compound (4) through a [1,3] sigmatropic hydride shift. Alternatively, compound (4) can be directly formed from the interaction of the $2\pi$ electrons in the triple bond with the $2\pi$ electrons in the maleimide double bond and a concomitant [1,5] sigmatropic hydride shift (Pathway b). To enhance thermo-oxidative stability, compound (4) is heat treated to achieve aromatization leading to compound (5). If a linear thermoplastic material is to be prepared, the synthesis must utilize stoichiometric quantities of the reactants. Otherwise, the presence of an excess reactant can result in the formation of semi-interpenetrating polymer networks.

There are precedents reported in the literature in which a triple bond conjugated with an aromatic ring is used as a diene system. Hudson and Robinson, for example, showed that when piperonyl-alkylene is allowed to react with maleic anhydride in xylene at 150° C. for two hours, an aromatic adduct is formed directly. This reaction is shown below.

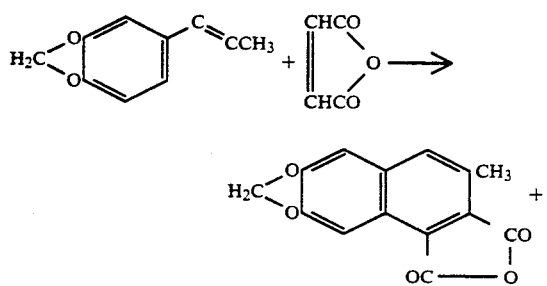

The most significant aspect of the present synthetic reaction resides in its potential to produce literally hundreds of new, tough, high performance polymeric materials, thereby advancing material technology. Such a broad applicability is due primarily to two factors.

One—at the present time there are a large number of acetylene-terminated materials, e.g., bismaleimides, biscitraconimides and benzoquinones which are available. They can be obtained either from commercial sources or prepared by a well-known synthetic method. The other factor is that these starting components can be reacted in a variety of combinations.

The reactivity of bisethynyl compounds varies and is structurally dependent. Likewise, the reactivity of bismaleimides, biscitraconimides and benzoquinones also differs from one compound to another, and is controlled by the nature of the particular structure.

Since the diene characterizes a donor in the Diels-Alder reaction, the reactivity of the diene system of the present invention is markedly enhanced when an electron-denoting substituent is present in the aromatic ring of a bisethynyl compound. Conversely, when an electron withdrawing group is present in the vicinity of the double bond in a bismaleimide, biscitraconimide or benzoquinone, the double bond is activated toward the Diel-Alder reaction.

To understand structure-property relationships for ATT polymers, a large number of ATT polymers have been synthesized and characterized. Tables 1 and 2 show the chemical structures and designations of the acetylene-terminated materials and the olefinic compounds, respectively. These starting materials were actually used to prepare a variety of ATT polymers using the synthetic reaction of the present invention. Among them, LaRC-RP 80 has been studied to the greatest extent. The synthesis and characterization of this new material demonstrate the utility of the present synthetic reaction.

TABLE 1

| Compound number | Structure of compound | Designation |
|---|---|---|
| I | | Thermid LR-600 |
| II | | Thermid FA-700 |
| III | | ETAE |
| IV | | m-ATS |
| V | | m-ATB |
| VI | | m-ATBZ |

TABLE 1-continued

| Compound number | Structure of compound | Designation |
|---|---|---|
| VII | (3-ethynylphenyl maleimide structure) | MA/PA |
| VIII | (3-ethynylphenyl phthalimide structure) | PhAT |
| IX | (phenylacetylene structure) | PA |
| 11 | (4,4'-bismaleimidodiphenylmethane structure) | MA/MDA |
| 12 | (bis-maleimido diphenyl sulfone structure) | MA/3,3'-DDS |
| 13 | (Kerimid 601 structure) | Kerimid 601 |

TABLE 1-continued

| Compound number | Structure of compound | Designation |
|---|---|---|
| 14 | (poly(maleimide-phenylmethylene-aniline)) structure | MA/PA |
| 15 | 3-ethynylphenyl maleimide structure | BQ |
| 16 | N-phenyl maleimide structure | MA/Ph |

TABLE 2

| Compound number | Structure of compound | Designation |
|---|---|---|
| 1 | | CA/MDA/6F |
| 2 | | CA/ODA/6F |
| 3 | | CA/DDS/6F |
| 4 | | CA/PD/6F |
| 5 | | CA/DAD/6F |
| 6 | | MA/MDA/6F |
| 7 | | MA/ODA/6F |
| 8 | | MA/DDS/6F |
| 9 | | MA/PDA/6F |

TABLE 2-continued

| Compound number | Structure of compound | Designation |
|---|---|---|
| 10 | (biscitraconimide structure with two maleimide end groups connected via -(CH2)12-N- linkers to phthalimide groups bridged by -C(CF3)2-) | MA/DAD/6F |

The ATT polymers of this invention are adapted for use as composite matrices and as adhesives and molding compounds suitable for aerospace structural applications in the 177° C. to 300° C. temperature range.

The following are examples that illustrate preparation and use of the ATT polymers for applications in advanced composites, as well as structural adhesives and molding articles. However, it is to be understood that these examples are merely illustrative and intended to enable those skilled in the art to practice the invention in all of the embodiments flowing therefrom, and do not in any way limit the scope of the invention as defined in the claims.

EXAMPLES

EXAMPLE 1

Synthesis and Characterization of LaRC-RP-80

1.1 Materials

Thermid LR-600 as a 50 weight percent solution in N,N-dimethylpyrrolidone (NMP) was purchased from National Starch. The 4,4'-methylenedianiline (MDA) from Eastman was used as received. The 2,2-bis(3,4-dicarboxyphenyl)hexafluoropropane dianhydride (6F) from American Hoechst was recrystallized from acetic anhydride/toluene (20/80 volume ratio), m.p. 245° C.-246° C. Citraconic anhydride (CA) from Aldrich was freshly distilled.

1.2 Synthesis of Biscitraconimide

The new biscitraconimide, CA/MDA/6F, the chemical structure of which is shown in Table 2, was prepared in two steps. Step one concerns the preparation of the diamine MDA/6F. Step two deals with the reaction of CA and MDA/6F according to the following procedure.

To a refluxing and stirred solution of the diamine MDA/6F (0.05 mole) in 200 ml of a solvent mixture consisting of methylene chloride and acetone in a 1:1 volume ratio, a solution of CA (0.1 mole) in 100 ml of the same solvent mixture was added over a 15 minute period. After refluxing for ten minutes, the reaction solution changed color from dark brown to yellow, and the solid material, identified to be the amic acid precursor, was precipitated. After one-half hour, sodium acetate (5 g) and acetic anhydride (100 ml) were added to chemically imidize the amic acid into the corresponding imide. Immediately following the addition of acetic anhydride and sodium acetate, the reaction solution changed color from yellow back to dark brown, and the solid material dissolved to give a clear brown solution. The progress of the reaction was followed by FTIR. After one hour the reaction product was worked up by washing three times with 200 ml of saturated sodium carbonate aqueous solution, drying the organic materials with anhydrous magnesium sulfate, and then evaporating the organic solvents. This afforded the crude biscitraconimide in 99% yield. After recrystallization from acetone/water, a light gray solid (overall yield 78%) was obtained, m.p. 190°-192° C. Its FTIR spectrum had the following characteristic absorption bands: 3100 (C=C—H maleimide), 1775 (C=O imide in-phase) and 1720 (C=O imide out-of-phase), 1635 (C=C maleimide), 1375, 1260, 1140, and 1100 cm$^1$ (C—F).

1.3 Resin Preparation and Characterization

Figure 2:
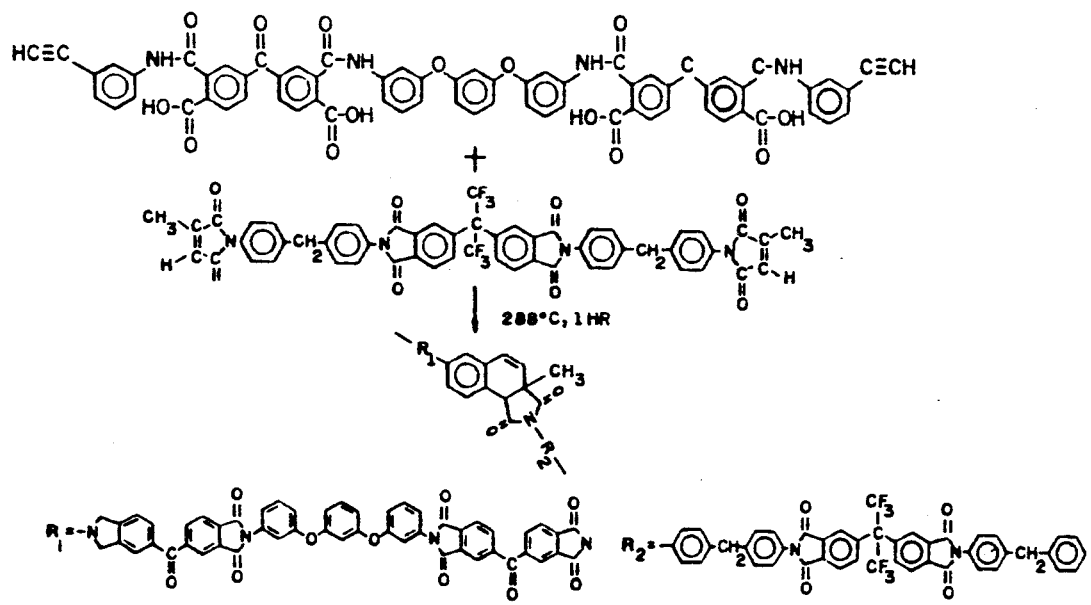
FIG. 2 is a reaction equation showing the synthesis of a polyimide product according to the present invention (LaRC-RP80) from a commercially available starting material (Thermid 600) and a novel monomeric material according to the present invention (CA/MDA/6F)

FIG. 2 shows the synthesis of LaRC-RP80. The commercial Thermid LR-600 (18.9 g, 0.008 mole) and the previously prepared CA/MDA/6F (8.0 g, 0.008 mole) were dissolved in 8 ml of acetone to give a 50% w/w dark brown solution. The solution was concentrated at 100° C. in a nitrogen atmosphere for one and one-half hours, followed by staging at 250° C. in air for one hour. This afforded LaRC-RP80 molding powder, the DSC of which showed one endotherm at 210° C. and one exotherm at 240° C. Interestingly, this exothermic peak was not found in the DSC scans of the Thermid 600 molding powder prepared under the same condition as LaRC-RP80 and CA/MDA/6F prepolymer. This suggests that this exotherm is due to the chemical structure resulting from the reaction of Thermid 600 with the biscitraconimide, rather than the homopolymerization of the constitutent materials. The LaRC-RP80 molding powder (15.50 grams) was placed in a cold matched metal die. This was then inserted into a press preheated to 288° C. A thermocouple was attached to the die to determine the temperature profile. When the die temperature reached 225° C., 2000 psi pressure was applied. The temperature was raised to 288° C. at a rate of 2° C./minute. The neat resin was cured at 288° C. in air under 2000 psi pressure for one hour and removed from the press when the die temperature cooled to 177° C. This afforded a neat resin having dimensions of 3.2 cm by 3.2 cm by 1.0 cm and a density of 1.35 g/cc. The optical microscopic examination of the cross-section of the neat resin showed no detectable voids or defects. This molding was then accepted for compact tension specimen preparation without postcuring. The compact tension testing was made according to ASTM G399 specifications. Unless otherwise noted, a fresh cut by a razor blade was made for each test specimen prior to its testing. Each value of the $G_{Ic}$ reported in this invention is an average of at least two determinations. For the other testing, however, the neat resin was postcured at 288° C. in air for four hours.

Table 3 shows the physical and mechanical properties of LaRC-RP80 while Table 4 gives some of the moisture absorption properties of this material.

TABLE 3

NEAT RESIN PROPERTIES OF LaRC-RP80

Physical Properties

TABLE 3-continued
NEAT RESIN PROPERTIES OF LaRC-RP80

| | |
|---|---|
| $Tg^1$, Dry/Wet$^2$, °C. | 268/254 |
| Density, g/cc | 1.33 |
| Moisture$^2$/Solvent$^3$ Absorption, % | 2.60/2.40 |
| Toughness | |
| $G_{Ic}$, J/m$^2$ (in-lbs/in$^2$)$^4$ | 338 (1.93) |
| Thermo-oxidative Stability by TGA in Air | |
| Onset temperature, °C. | 484 |
| Temperature at 5% wt loss, °C. | 514 |
| Wt loss after 50 hours at 371° C., % | 18 |

$^1$Determined by TMA.
$^2$Specimens immersed in water at room temperature for two weeks.
$^3$Specimens immersed in boiling CH$_2$Cl$_2$ for 60 hours.
$^4$Calculated from $K_{Ic}$ using Thermid 600 tensile modulus at room temperature 6.0 × 10$^5$ psi, average of two runs with variability 3%.

TABLE 4
Moisture Absorption of ATT Polymers Compared with Commercial Products

| Resin | Tg, °C.$^a$ Wet | Moisture Uptake$^b$ Wt. % |
|---|---|---|
| LaRC-RP80 | 254 | 2.6 |
| LaRC-RP83 | 249 | 2.1 |
| Thermid 600 TM (National Starch) | — | 1.2 |
| Kerimid 601 (Rhone-Poulenc) | — | 4.5 |

$^a$By TMA at a heating rate of 5° C./min.;
$^b$Two weeks in water at 25° C.

1.4 Adhesive Bonding and Testing

The resin solution from Example 1.3 was brush coated onto a 112 E-glass (A1100 finish) cloth which was stretched over a metal frame. The scrim cloth was dried between coatings at 60° C. in air for one-half hour. After the fourth coating, the cloth was staged at 100° C., 150° C. and 177° C. in air for one hour at each temperature. Single lap shear bond specimens were prepared using 25.4 mm wide, 1.27 mm thick 6Al-4V titanium adherends. The bond area of the adherend was surface treated with Pasa Jell 107, which is marketed by SEMCO, Glendale, Calif., primed with the resin solution and heated in the same manner as the scrim cloth prepared above. Sandwiching the β-staged scrim cloth between the primed adherends having a 12.7 mm overlap, the lap shear specimens were bonded as follows: (1) raise temperature from room temperature to 250° C. at 4° C./min, (2) apply 200 psi at 250° C. and raise temperature to 288° C. at 4° C./min, (3) hold one hour at 288° C. under 200 psi pressure and (4) cool to room temperature under pressure. The bonded specimens were postcured at 288° C. in air for four hours. The lap shear tests were performed on an Instron universal testing machine according to ASTM D-1002.

Table 5 lists the adhesive properties.

1.5 Reaction Mechanisms

Figure 3:
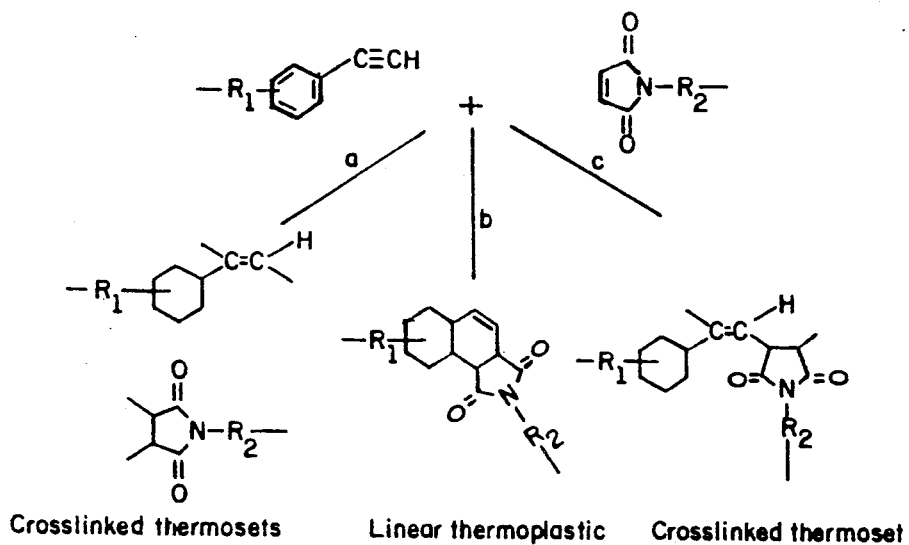
FIG. 3 is a reaction equation showing possible mechanisms for the reaction of a bisethynyl compound with a bismaleimide.

FIG. 3 shows that the reaction of an acetylene terminated compound with a maleimide can occur in three ways: (a) the individual homopolymerization of each of the two reactants leads to a mixture of crosslinked networks; (b) the cycloaddition reaction of the acetylene with the maleimide forms an ATT via one of the two routes shown in FIG. 1; and (c) the addition of the maleimide double bond across the acetylene triple bond gives a highly crosslinked material. Only pathway (b) forms a tough linear thermoplastic material. The other two routes produce brittle crosslinked polymers. This is an important distinction.

1.6 Evidence for ATT

Figure 4:
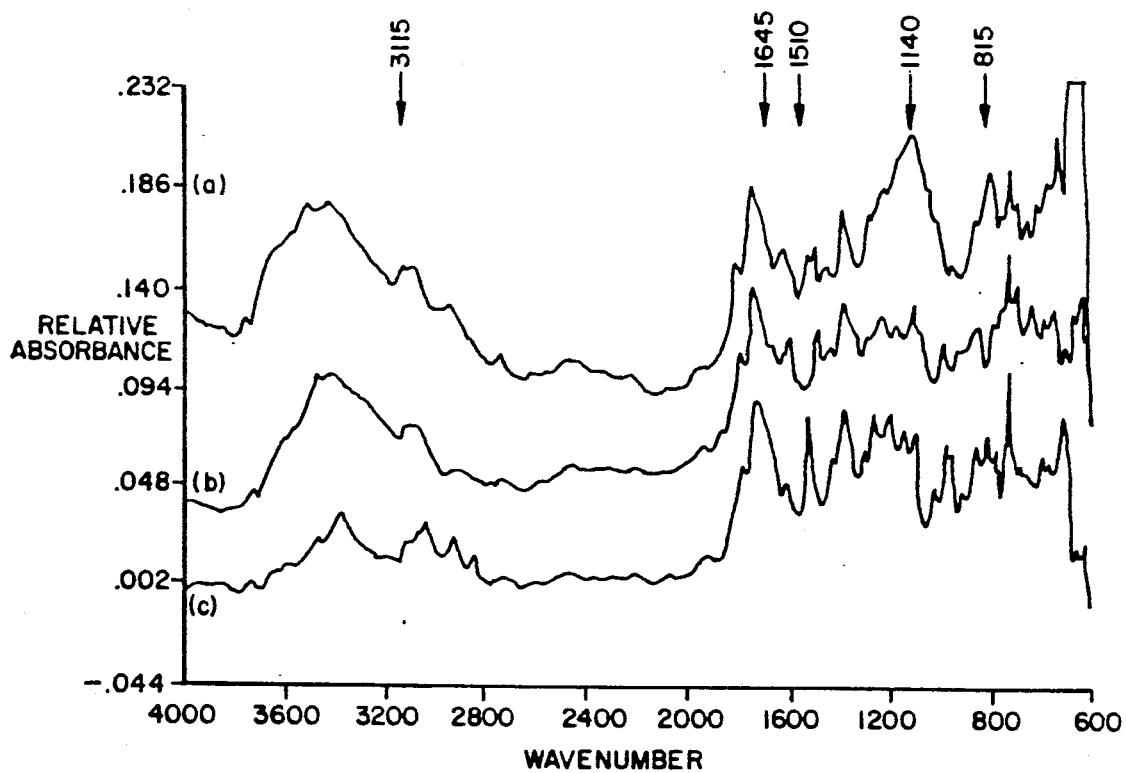
FIG. 4 shows FTIR spectra of (a) the polyimide product of FIG. 2, in accord with the present invention, (b) the commercially available starting material of FIG. 2, and (c) the novel monomeric material of FIG. 2, in accord with the present invention.

Of the above three reaction mechanisms set forth in FIG. 3, pathway (b) is consistent with the following five findings. First, the FTIR spectrum of cured LaRC-RP80 neat resin showed five new absorption bands which are consistent with the formation of a cycloaddition adduct. These new bands are marked with an arrow shown in FIG. 4. For comparison purposes, the FTIR spectra of Thermid 600 and CA/MDA/6F polymers cured under the identical condition as LaRC-RP80 are also shown in FIG. 4. The new bands and their assignments are 3115 cm$^{-1}$ due to stretching vibration of C=C—H in cyclohexene, 1645 cm$^{-1}$ due to stretching vibration of C=C in cyclohexene, 1510 cm$^{-1}$ due to aromatic ring adjacent to cyclohexene, 1140 cm$^{-1}$ due to C—N—C succinimide. Next LaRC-RP80 is significantly tougher than the constituent polymers ($G_{Ic}$ 338 J/m$^2$ compared to 93 J/m$^2$ for Thermid 600). Such high toughness characteristics are in line with the behavior of a linear thermoplastic, but not with the behavior of a highly crosslinked polymer. Third, the DSC scan of LaRC-RP80 molding powder shows an exothermic peak around 240° C., which is not seen in the DSC scans of the constituent materials. This suggests that pathways (b) and (c), but not (a), are occurring. Fourth, only one Tg was observed in the TMA thermogram (see FIG. 5) and confirmed in the TBA spectrum of LaRC-RP80. From this, it follows that LaRC-RP80 is a one-phase system. Such a morphology is consistent with both pathways (b) and (c), but not (a). Finally, AS-4/LaRC-RP80 composite can be reprocessed to correct flaws.

On the basis of the foregoing discussion, the evidence supporting the formation of an ATT through pathway (b) is strong. A model compound study is underway to clarify the reaction mechanism.

TABLE 5
ADHESIVE PROPERTIES
Lap Shear Strength, MPa (psi) Titanium-to-Titanium

| Resin | 25° C. Dry | 25° C. Wet | 232° C. Dry | 232° C. Wet | Aged* |
|---|---|---|---|---|---|
| LaRC-RP80 | 14.3 (2078) | 20.5 (2975) | 19.2 (2786) | 20.5 (2963) | 12.6 (1820) |
| LaRC-RP80-A | 13.8 (2004) | 16.8 (2440) | — | 9.5 (1375) | 8.9 (1283) |
| LaRC-RP83 | 16.9 (2446) | 21.1 (3063) | 20.5 (2975) | 20.4 (2950) | 10.5 (1528) |
| LaRC-RP83-A | 14.0 (2034) | 16.9 (2450) | 17.6 (2552) | 17.0 (2465) | 17.2 (2493) |
| Thermid 600 TM (National Starch) | 10.5 (1515) | — | 15.5 (2243) | — | — |
| Kerimid 601 TM (Rhone-Poulenc) | 8.3 (1210) | — | 4.3 (620) | — | — |

1.7 Processing

State-of-the-art BMIs are known for their ease of processing. However, their processing cycles often require long curing and postcuring time involving several steps. LaRC-RP80 can be processed easily and quickly for the following three reasons. The reacting components are readily soluble in a low boiling solvent, such as acetone, making solvent removal easy. It has an addition curing mechanism, which eliminates voids caused by evolution of volatile by-products during the critical final stage of curing. Lastly, the curing takes place rapidly at a moderately high temperature. Table 6 shows a standard cure cycle used for the ATT polymers of the present invention and compares the same with a typical cure cycle adapted for a commercial product.

TABLE 6

ADHESIVE PROPERTIES OF LaRC-RP80 AND THERMID 600 TITANIUM-TO-TITANIUM

| Resin | Lap Shear Strength. MPa (psi)[1] | | | | |
|---|---|---|---|---|---|
| | RT | | 232° C. | | |
| | Dry[3] | Wet[4,5] | Dry[6] | Wet[6] | Aged[4,7] |
| LaRC-RP802 | 14.3 (2078) | 20.5 (2975) | 19.2 (2786) | 20.5 (2963) | 12.6 (1820) |
| Thermid 600 | 10.5 (1515) | — (2243) | 15.5 | — | — |

[1]Average of four tests with variability 6%; average bondline thickness 0.005".
[2]Fracture surfaces are smooth without visible voids.
[3]Failure adhesive.
[4]Failure cohesive/adhesive.
[5]Specimen immersed in water at room temperature for two weeks.
[6]Failure cohesive.
[7]After aging for 500 hours at 288° C. in air.

1.8 Resin Properties

As shown in FIG. 5, LaRC-RP80 had dry and wet Tgs at 268° C. and 254° C., respectively. Isothermal aging at 371° C. in air for four hours increased the Tg to 312° C. While having a high Tg, LaRC-RP80 also showed exceptional toughness characteristics. The value of $G_{Ic}$ was found to be 338 J/m$^2$. Since high toughness and high Tg are desirable properties, and because the former is often achieved at the expense of the latter, it is interesting to compare both of the properties simultaneously. The values of $G_{Ic}$ for state-of-the-art BMIs having Tgs in the range of 230° C. to 290° C. vary from 34 to 260 J/m$^2$. FIG. 6 shows the scanning electron micrograph of the fracture surface of LaRC-RP80. The fractography of LaRC-RP80 reveals a dendritic pattern. The initial propagation region shows extended arrays and lines which run in the direction of crack propagation and extend over a considerable distance with a high degree of regularity. The fracture surface morphology of LaRC-RP80 is in striking contrast with the smooth and mirror-like morphology of Thermid 600 material.

As shown in FIG. 7, LaRC-RP80 has a 5% weight loss temperature of 514° C. This represents the highest thermo-oxidative stability ever observed for BMIs developed to date. In addition, the data of FIG. 7 and FIG. 8 indicate that the thermo-oxidative stability of LaRC-RP80 is equivalent to that of Thermid 600, and is substantially better than that of the biscitraconimide CA/MDA/6F.

LaRC-RP80 also exhibited outstanding moisture resistance (Table 4). Typical BMIs have equilibrium moisture absorptions which range from four to six percent. A value of 2.6 percent was obtained for LaRC-RP80. The good moisture resistant characteristics of this material are reflected in the high wet Tg mentioned previously and the excellent hot/wet lap shear strength presented below in Table 5.

1.9 Adhesive Properties

Adhesive properties are summarized in Table 5. The room temperature lap shear strength of LaRC-RP80 was 2078 psi, using titanium as an adherend. Moisture absorption increases the lap shear strengths at both room temperature and elevated temperature. Moreover, elevated temperature tests also resulted in higher lap shear strengths for both dry and wet conditions. This was unexpected. Invariably, the specimens tested at room temperature in dry conditions showed adhesive failure, whereas the moisture saturated samples tested at 232° C. showed cohesive failure. With 2963 psi lap shear strength at 232° C. in wet condition, LaRC-RP80 retains 143 percent of its room temperature properties. State-of-the-art BMIs have considerably poorer adhesive properties by comparison.

EXAMPLE 2

Reproducibility Study

To evaluate the reproducibility of the neat resin properties for LaRC-RP80, another molding of LaRC-RP80 composition was prepared and tested in the same manner as in Example 1.3. The $G_{Ic}$ value from the first experiment was found to be 324 J/m$^2$. This is to be compared with a value of 338 J/m$^2$ obtained from the second experiment. Other testing results comparing two experiments were also found to be in excellent agreement.

EXAMPLE 3

Preparation of LaRC-RP80A

According to the mechanism proposed for the present synthetic reaction, a highly linear polymer is predicted when a stoichiometric quantity of each reactant is used. An off-stoichiometric composition would lead to a more brittle material. To test this hypothesis, a polymer was prepared from 18.9 g of the Thermid LR-600 solution (0.008 mole) and 5.3 g of CA/MDA/6F (0.005 mole). This composition was evaluated in the form of an adhesive. As shown in Table 5, the adhesive properties for this off-stoichiometric composition are considerably inferior to those of the stoichiometric counterpart, namely, LaRC-RP80. A similar trend was also observed in LaRC-RP83 and LaRC-RP83A as described below.

EXAMPLE 4

Synthesis and Characterization of LaRC-RP83

A 50 weight percent resin solution was prepared by stirring 8.0 g (0.008 mole) of CA/ODA/6F, 18.9 g (0.008 mole) of the Thermid LR-600 solution and 8 ml of acetone at room temperature for one hour. For a molding application, the procedure of Example 1.3 was followed, resulting in a void-free neat resin with a density of 1.37 g/cc. Table 7 summarizes the physical and mechanical properties of the ATT polymers including LaRC-RP83.

The above resin solution was also used to prepare titanium-to-titanium single lap shear joints following the procedure described in Example 1.4. The adhesive properties for LaRC-RP83 are given in Table 5.

TABLE 7

Neat Resin Properties of ATT Polymers Prepared from Thermid LR-600 and Bismaleimides, Biscitraconimides or Benzoquinone

| Resin System | Composition[1] Bisethynyl Compound | Composition[1] Bidmaleimide or Other | Tg, °C[2] TMA[3] | Tg, °C[2] DSC[4] | TGA[5] Temperature at 5% wt. loss, °C | Fracture Toughness[6] $K_{1C}$, Psi-in$^{\frac{1}{2}}$ | Fracture Energy[7] $G_{1C}$, J/m$^2$ | Relative[8] Toughness |
|---|---|---|---|---|---|---|---|---|
| LaRC-RP 80 | Thermid LR-600 | CA/MDA/6F | 268 | — | 514 | 1076 | 338 | 10.0 |
| LaRC-RP 83 | Thermid LR-600 | CA/ODA/6F | 248 | — | 455 | 882 | 227 | 6.7 |
| LaRC-RP 56 | Thermid LR-600 | CA/DDS/6F | 272 | 275 | 440 | 186 | 10 | 0.3 |
| LaRC-RP 57 | Thermid LR-600 | CA/PD/6F | 245 | — | 440 | 2076[9] | 1257 | 37.0 |
| LaRC-RP 98 | Thermid LR-600 | MA/MDA/6F | 262 | 265 | 430 | 742 | 161 | 4.7 |
| LaRC-RP 99 | Thermid LR-600 | MA/ODA/6F | 245 | 252 | 435 | 763 | 170 | 5.0 |
| LaRC-RP 100 | Thermid LR-600 | MA/DDS/6F | 250 | 250 | 395 | crack[10] | — | — |
| LaRC-RP 101 | Thermid LR-600 | MA/PD/6F | 255 | 252 | 385 | 752 | 165 | 4.9 |
| LaRC-RP 103 | Thermid LR-600 | P-Benzoquinone | 250 | 248 | 485 | 929 | 252 | 7.4 |
| LaRC-RP 104 | Thermid LR-600 | Kerimid 601 | 270 | 290 | 465 | 1064 | 330 | 9.7 |

[1]Cured 2 hrs at 288° C.;
[2]Post-cured 4 hrs at 288° C.;
[3]By TMA at a heating rate of 5° C./min;
[4]By DSC at a heating rate of 10° C./min;
[5]By TGA at a heating rate of 2.5° C./min in air;
[6]Per ASTM E399;
[7]Calculated from $G_{1C} = K_{1C}^2/E$, using Thermid LR = 600 tensile modulus E = 6.0 × 10$^5$ Psi;
[8]Compared to commercial bismaleimide, Kerimid 601;
[9]No razor blade cut, the others in Table 1 had a fresh razor blade cut prior to compact tension testing;
[10]Cracked prior to testing.

EXAMPLE 5

Preparation of LaRC-RP83A

As in Example 3, a polymer having a 1.5:1.0 mole ratio of Thermid LR-600 to CA/ODA/6F was prepared from mixing 18.9 g of the Thermid LR-600 solution with 5.3 g of CA/ODA/6F. This polymer was evaluated in the form of an adhesive.

EXAMPLE 6

Synthesis and Characterization of LaRC-RP56

To 18.89 g (0.0081 mole) of the Thermid LR-600 solution were added 8.86 g (0.0081 mole) of CA/DDS/6F and 15 mole of acetone. The mixture was stirred at about 45° C. for 15 minutes to give a gray solution which was dried at 150° C. in air for one hour and then under vacuum (30-inch Hg) for another hour at 150° C. The dried material showed excessive flow. To reduce the resin flow, the material was staged at 200° C. in air for one-half hour. About 17.1 g of the staged molding powder was cured two hours at 288° C. under 2000 psi pressure. This afforded a neat resin having a density of 1.29 g/cc. Voids were apparent in all of the neat resin surfaces.

Example 7

Synthesis and Characterization of LaRC-RP57

As in Example 6, 6.60 g (0.0081 mole) of CA/PD/6F and 5 ml of acetone were added into 18.89 g (0.0081 mole) of the Thermid LR-600 solution. This yielded a void-free neat resin having a density of 1.33 g/cc. Normally, a fresh razor blade cut was made on all of the compact tension specimens prior to testing. However, no razor blade cut was given to LaRC-RP57 specimens. This is reflected in the $G_{Ic}$ value of 1257 J/m$^2$ shown in Table 7. This value is higher than an expected value if a fresh razor blade cut had been made prior to testing.

Example 8

Synthesis and Characterization of LaRC-RP98

To 18.89 g (0.0081 mole) of the Thermid LR-600 solution was added 8.00 g (0.0081 mole) of MA/M-PA/6F and 15 ml of acetone. The cured resin showed no voids or defects and had a density of 1.34 g/cc.

Example 9

Synthesis and Characterization of LaRC-RP99

To 18.89 g of the Thermid LR-600 solution were added 8.0 g of MA/ODA/6F and 15 ml of acetone. The resulting neat resin showed no apparent voids and had a density of 1.36 g/cc.

Example 10

Synthesis and Characterization of LaRC-RP100

To 18.89 g of the Thermid LR-600 solution were added 8.0 g of MA/DDS/6F and 15 ml of acetone. The neat resin cracked during machining of its compact tension specimen, which is indicative of brittleness. The resin had a density of 1.33 g/cc and showed no voids.

Example 11

Synthesis and Characterization of LaRC-RP101

To 18.89 g of the Thermid LR-600 solution was added 8.0 g of MA/PD/6F and 15 ml of acetone. The cured neat resin showed no voids and had a density of 1.38 g/cc.

Example 12

Synthesis and Characterization of LaRC-RP103

About 3.49 g (0.0323 mole) of P-benzoquinone (Aldrich Chemicals) was mixed with 73.55 g (0.0323 mole) of the Thermid LR-600 solution at room temperature for one hour. The solution was concentrated at 169° C. for two hours under vacuum (30-inch Hg) to give a black solid material. To reduce the flow, the material was staged at 200° C. for one hour in air. Because of the high flow of the molding powder, a pressure of 200 psi was used instead of the standard 2000 psi pressure used for the other moldings. After curing at 288° C. for two

Example 14

Synthesis and Characterization of LaRC-RP105

A resin solution was prepared by stirring 13.97 g (0.0104 mole) of the preimidized Thermid FA-700 yellow powder (National Starch), 10.0 g (0.0104 mole) of MA/MDA/6F and 150 ml of methyl ethyl ketone(MEK) at room temperature for one hour. The resulting dark brown solution was concentrated at 60° C. under vacuum (30 inches Hg) for one-half hour and then staged at 200° C. in air for 25 minutes. This yielded a void-free neat resin having a density of 1.35 g/cc. Table 8 summarizes the neat resin properties.

TABLE 8

Neat Resin Properties of ATT Polymers Prepared from Other Bisethynyl Compounds and Bismaleimides, Biscitraconimides or Benzoquinone

| Resin System | Composition[1] | | $T_g$, °C.[2] | | TGA[5] Temperature at 5% wt. loss, °C. | Fracture Toughness[6] $K_{1C}$, Psi-in$^{\frac{1}{2}}$ | Fracture Energy[7] $G_{1C}$, J/m$^2$ | Relative[8] Toughness |
|---|---|---|---|---|---|---|---|---|
| | Bisethynyl Compound | Bidmaleimide or Other | TMA[3] | DSC[4] | | | | |
| LaRC-RP 105 | Thermid FA-700 | MA/MDA/6F | 255 | 255 | 435 | 1378 | 554 | 16.3 |
| LaRC-RP 106 | Thermid FA-700 | CA/MDA/6F | 230 | — | 473 | 1689 | 832 | 24.5 |
| LaRC-RP 107 | Thermid FA-700 | Kerimid 601 | 265 300 | — 308 | 470 | 673 | 132 | 3.9 |
| LaRC-RP 108 | Thermid FA-700 | P-Benzoquinone | 290 | 275 | — | 935 | 255 | 7.5 |
| LaRC-RP 109 | ETAE | CA/MDA/6F | 262 | 260 | 470 | 1755 | 898 | 26.4 |
| LaRC-RP 110 | m-ATS | CA/MDA/6F | 240 | 239 | 442 | 330[9] | 32 | 1.0 |
| LaRC-RP 111 | m-ATS | Kerimid 601 | 320 | 320 | 390 | 472 | 65 | 1.9 |
| LaRC-RP 112 | m-ATB | CA/MDA/6F | 230 | 230 | 425 | crack[10] | — | — |
| LaRC-RP 113 | m-ATB | Kerimid 601 | 290 | 300 | 420 | 288 | 24 | 0.7 |
| LaRC-RP 114 | MA/PA | P-Benzoquinone | >350 | | — | — | — | — |
| LaRC-RP 115 | PhAT | MA/Ph | >350 | | — | — | — | — |
| LaRC-RP 116 | PA | MA/MDA | 321 | | 390 | — | — | — |

See Table 1 for footnotes 1 through 10.

hours under 200 psi pressure, a neat resin was obtained which showed voids and a density of 1.0 g/cc. Such a low density suggests that the material was not consolidated properly. To see if the neat resin could be reprocessed to correct its flaws, the resin was treated at 300° C. for ten minutes under 3000 psi pressure. This produced a neat resin the density of which increased from 1.0 g/cc to 1.33 g/cc. Also, the reprocessed material showed no voids. From these results, it can be inferred that an ATT polymer is reprocessable.

Example 13

Synthesis and Characterization of LaRC-RP104

About 58.78 g of the Thermid LR-600 solution was added into a solution of 20.5 g of Kerimid 601 powder (Rhone Poulenc) in 30 ml of NMP. After stirring at room temperature for one hour, the solution was concentrated at 150° C. for three hours under vacuum (30-inch Hg). To reduce flow, the material was staged at 200° C. for 15 minutes. The cured resin showed some voids and had a density of 1.25 g/cc. The material had a two-phase morphology with surfaces showing a blending of brown and gold colored materials.

Example 15

Synthesis and Characterization of LaRC-RP106

About 13.97 g (0.0104 mole) of the Thermid FA-700 powder, 10.34 g (0.0104 mole) of CA/MDA/6F and 50 ml of acetone was stirred at room temperature for one hour to give a dark brown solution. The solution was concentrated at 149° C. in air for one hour. The pale white solids were staged at 200° C. for one-half hour. The cured resin showed no voids and had a density of 1.36 g/cc.

Example 16

Synthesis and Characterization of LaRC-RP107

A mixture of 16.0 g of the Thermid FA-700 powder, 5.1 g of Kerimid 601 powder and 30 ml of acetone was stirred at room temperature for one hour to give a red-brown solution. This solution was concentrated at 60° C. in air for one hour and then staged at 200° C. for one-half hour. The resulting void-free neat resin had a density of 1.35 g/cc.

Example 17

Synthesis and Characterization of LaRC-RP108

The mixture of 13.97 g (0.0104 mole) of the Thermid FA-700 powder, 1.13 g (0.0104 mole) of P-benzoquinone and 30 ml of acetone was stirred at room temperature for one hour to produce a brown solution. After concentration and staging at 200° C. for one-half hour, the molding powder was cured following the standard cure cycle given in Table 6. This resulted in a neat resin having a density of 1.29 g/cc. The surfaces showed some voids but no cracks.

Example 18

Synthesis and Characterization of LaRC-RP109

A mixture of 7.81 g (0.001 mole) of ETAE (Mn 8000, ηinh 0.36 dl/g, Tg 252° C.), 0.97 g (0.001 mole) of CA/MDA/6F and 50 ml of chloroform was stirred at room temperature for one hour to give a yellow-green solution. The solution was concentrated at 150° C. in air for 45 minutes. The molding powder showed limited flow and, thus, 3000 psi pressure was used to consolidate the molding. This produced a mirror-like, smooth, and void-free molding. Surprisingly, it had a low density of 1.21 g/cc.

EXAMPLE 19

Synthesis and Characterization of LaRC-RP110

A mixture of 5.05 g of m-ATS (Hysol-Dexter), 10.0 g of CA/MDA/6F, and 20 ml of acetone was stirred at room temperature for one hour to give a dark brown solution. The solution was concentrated at 126° C. for one hour and then staged at 288° C. for ten minutes. This afforded a neat resin which showed no voids or cracks and had a density of 1.30 g/cc.

Example 20

Synthesis and Characterization of LaRC-RP111

A mixture of 8.30 g of m-ATS (Hysol-Dexter), 8.30 g of Kerimid 601 and 30 ml of acetone was stirred at room temperature for one hour to give a yellow solution. The solution was concentrated at 126° C. for one and one-half hours and then staged at 225° C. for ten minutes. The neat resin had a density of 1.20 g/cc. Like LaRC-RP107, this molding also showed a two-phase morphology.

Example 21

Synthesis and Characterization of LaRC-RP 112

To a solution of 5.0 g (0.0101 mole) of m-ATB (Hysol-Dexter) in 15 ml of acetone was added 10.0 g (0.0101 mole) of CA/MDA/6F. After stirring at room temperature for one hour, the resulting brown solution was concentrated at 150° C. for two hours. To reduce flow, the dried material was staged at 200° C. for one hour. The cured resin had a density of 1.27 g/cc and showed no voids or defects. However, the four compact tension specimens were cracked during cutting with a sharp razor blade.

Example 22

Synthesis and Characterization of LaRC-RP113

A mixture of 8.30 g of m-ATB (Hysol-Dexter), 8.30 g of Kerimid 601 and 30 ml of acetone was stirred at room temperature for one hour to give a brown solution. The solution was concentrated at 126° C. for one hour and then staged at 200° C. for five minutes. The staged material strongly adhered onto a beaker and was difficult to remove from the beaker. The curved resin had a density of 1.14 g/cc and showed a considerable number of voids.

Example 23

Synthesis and Characterization of LaRC-RP114

Monomeric MA/PA (4.0 g, 0.0203 mole) prepared by a standard method in our laboratory was allowed to react with P-benzoquinone (1.10 g, 0.0102 mole) in xylene at 144° C. for 24 hours. After cooling to room temperature, brown solid materials precipitated from the solution and were filtered and dried. The material showed no detectable Tg up to 350° C. Moreover, its FTIR spectrum showed a new band around 1639 cm$^{-1}$, which is about 20 cm$^{-1}$ lower than the absorption at 1659 cm$^{-1}$ due to the carbonyl group of P-benzoquinone.

Example 24

Synthesis and Characterization of LaRC-RP115

Monomeric PA (0.57 g, 0.006 mole) and MA/MDA (1.0 g, 0.003 mole) were allowed to react in a solid state at 250° C. for one hour.

Example 25

Synthesis and Characterization of Constituent Materials

Since many processing parameters are known to significantly affect the properties of a polymeric material, a comparison of material properties would be meaningless, unless the materials are prepared and tested under identical conditions. For this reason, molding compounds of constituent materials including Thermid LR-600, Thermid FA-700, CA/MDA/6F, CA/PD/6F, CA/DDS/6F, MA/MDA/6F, MA/ODA/6F, MA/PD/6F, and MA/DDS/6F were prepared and tested along with the ATT materials under carefully controlled conditions. Their neat resin properties are summarized in Table 9.

TABLE 9

| Constituent Material[1] | | Neat Resin Properties of Constituent Materials | | | | | |
|---|---|---|---|---|---|---|---|
| | | Tg, °C.[2] | | TGA[5] Temperature at 5% wt. loss, °C. | Fracture Toughness[6] $K_{1C}$, Psi-in$^{\frac{1}{2}}$ | Fracture Energy[7] $G_{1C}$, J/m$^2$ | Relative[8] Toughness |
| Bisethynyl Compound | Bidmaleimide or Other | TMA[3] | DSC[4] | | | | |
| Thermid LR-600 TM (National Starch) | — | 305 | — | 514 | 563 | 93 | 2.7 |
| Thermid FA-700 TM (National Starch) | — | 230 | 242 | 485 | 958 | 268 | 7.9 |
| m-ATS TM (Hysol-Dexter) | — | 360[11] | — | — | — | 3.5[11] | 0.1 |
| m-ATB TM (Hysol-Dexter) | — | 275[11] | — | — | — | 3.5[11] | 0.1 |
| — | Kerimid 601 | 290[12] | | 347[12] | 348[12] | 34[12] | 1.0 |

TABLE 9-continued

| Constituent Material[1] | | Neat Resin Properties of Constituent Materials | | | | | |
|---|---|---|---|---|---|---|---|
| Bisethynyl Compound | Bidmaleimide or Other | Tg, °C[2] | | TGA[5] Temperature at 5% wt. loss, °C | Fracture Toughness[6] $K_{1C}$, Psi-in$^{\frac{1}{2}}$ | Fracture Energy[7] $G_{1C}$, J/m² | Relative[8] Toughness |
| | | TMA[3] | DSC[4] | | | | |
| — | TM (Rhone-Poulenc) CA/MDA/6F | 230 | 231 | 400 | 497[9] | 72 | 2.1 |
| — | CA/ODA/6F | — | — | — | — | — | — |
| — | CA/PD/6F | 302 | 310 | 380 | crack[10] (extremely brittle) | — | — |
| — | CA/DDS/6F | 300 | 322 | 420 | crack[10] (extremely brittle) | — | — |
| — | MA/MDA/6F | 251 | 250 | 405 | 34 | 0.34 | 0.01 |
| — | MA/ODA/6F | 290 | 300 | 410 | 864[9] | 218 | 6.4 |
| — | MA/PD/6F | 310 | 322 | 365 | crack[10] (extremely brittle) | — | — |
| — | MA/DDS/6F | 350 | 345 | 390 | crack[10] (extremely brittle) | — | — |

See Table 1 for footnotes 1 through 10;
[11] Reported by Y. P. Sachdeva and S. E. Wentworth, to be published by J. Adhesion;
[12] Reported by D. A. Scola and D. J. Parker, Proceedings of the 1985 SPE ANTEC, 399 (1985).

Example 26

Preparation of Celion 6000/LaRC-RP104

A 40 weight percent resin solution was prepared by stirring 117.56 g of the Thermid LR-600 solution, 41.0 g of Kerimid 601 and 90.89 g of NMP at 60° C. for two hours. A prepreg was prepared by passing a single tow of unsized Celion 6000 graphite fiber through the resin solution contained in a dip tank and onto a 12-inch diameter multiple speed drum winder wrapped with release paper. This afforded a 23.5 cm by 190 cm wet prepreg. By visual inspection, the wet prepreg showed good drape and tack characteristics. The tape was dried on the rotating drum at room temperature for 16 hours, removed from the drum and cut into 7.6 cm by 17.8 cm plies. Twelve plies were stacked unidirectionally and then staged at 150° C. for one hour in a air-circulating oven. The staged lay-up was placed in a cold matched metal die. This was then inserted into a press preheated to 204° C. A thermocouple was attached to the matched die to determine the temperature. When the die temperature reached 177° C., 200 psi pressure was applied. The composite was cured one-half hour at 204° C., one hour at 250° C. and one hour at 288° C. under 200 psi pressure, and then removed from the press when the die temperature reached 150° C. The composite was then postcured at 288° C. for four hours in an air-circulating oven. An ultrasonic C-scan of the composite showed no detectable voids or defects and, therefore, the composite was accepted for test specimen preparation. The composite was found to contain 47 weight percent resin. The properties shown in Table 10 have not been normalized. For comparison purposes, a Celion 6000/Kerimid 601 composite was also fabricated and tested along with the ATT counterparts.

TABLE 10

| | Unidirectional Composite Properties of ATT Polymers Compared with Constituent Materials | | | | | | | |
|---|---|---|---|---|---|---|---|---|
| Composite | Density g/cm³ | Tg, °C[a] | Flexural Strength, Ksi[b,c] | | Flexural Modulus, Msi[b,c] | | Interlaminar Shear Strength, Ksi[c,d] | |
| | | | 25° C. | 232° C. | 25° C. | 232° C. | 25° C. | 232° C. |
| Celion 6000/ LaRC-RP104 | 1.53 | 310 | 232 | 173 | 13.6 | 12.8 | 17.6 | 11.8 |
| Celion 6000/ LaRC-RP117 | 1.61 | 230, 340 | 387 | 232 | 25.1 | 22.2 | 12.0 | 6.6 |
| Celion 6000/ LaRC-RP118 | 1.50 | 245, 305 | 340 | 210 | 18.0 | 17.0 | — | — |
| Celion 6000/ Kerimid 601 TM (Rhone-Poulenc) | 1.52 | 313 | 284 | 229 | 16.9 | 17.3 | 15.4 | — |

[a] By TMA;
[b] Per ASTM D790;
[c] Each value is an average of three determinations;
[d] Per ASTM D2344

Example 27

Preparation of Celion 6000/LaRC-RP117

As in example 26, a 40 weight percent resin solution was prepared from 117.56 g of the Thermid LR-600 solution, 18.0 g of MA/MDA (Aldrich Chemical), and 56.39 g NMP. This resin solution was used to fabricate a high quality composite.

Example 28

Preparation of Celion 6000/LaRC-RP118

As in Example 26, a 40 weight percent resin solution was prepared by mixing 117.56 g of the Thermid LR-600 solution, 20.50 g of MA/3,3'-DDS and 60.14 g of NMP. This resulted in a void-free composite.

Example 29

Reproducibility Study of Composite Fabrication

In order to assess the reproducibility of the composite properties, four composite panels, each having dimensions of 7.62 cm by 15.24 cm by 0.18 cm were fabricated using the resin solution and procedure set forth in Example 26. The results of this reproducibility study are summarized in Table 11. From a comparison of the properties presented in Table 11, it is evident that the reproducibility of properties for LaRC-RP104 composite is excellent.

1.91 cm by 0.15 cm was fabricated for each of the following seven matrix systems: LaRC-RP80, LaRC-

TABLE 11

Reproducibility of Composite Mechanical Properties of Celion 6000/LaRC-RP104

| Composite Number | Density g/cm³ | Flexural Strength, Ksi | | Flexural Modulus, Msi | | Interlaminar Shear Strength, Ksi | |
|---|---|---|---|---|---|---|---|
| | | 25° C. | 232° C. | 25° C. | 232° C. | 25° C. | 232° C. |
| First | | 216 | 121 | 14.4 | 11.4 | 9.7 | 14.7 |
| | | 195 | 113 | 13.1 | 12.2 | 10.2 | 14.9 |
| | | 228 | 156 | 13.9 | 12.0 | 13.2 | 13.3 |
| | Ave. | 213 | 130 | 13.8 | 11.9 | 11.0 | 14.3 |
| Second | | 221 | 112 | 14.8 | 11.7 | 12.0 | — |
| | | 189 | 151 | 13.4 | 13.2 | 13.5 | — |
| | | 246 | 125 | 13.4 | 12.5 | 13.2 | — |
| | Ave. | 219 | 130 | 13.9 | 12.5 | 13.0 | — |
| Third | | 223 | 186 | 13.4 | 12.9 | 17.4 | 9.3 |
| | | 231 | 171 | 13.6 | 13.3 | 17.9 | 17.7 |
| | | 241 | 162 | 13.9 | 12.2 | 17.5 | 8.4 |
| | Ave. | 232 | 173 | 13.6 | 12.8 | 17.6 | 11.8 |
| Fourth | | 193 | 130 | 10.4 | — | 17.9 | 11.0 |
| | | 196 | 136 | — | — | 17.6 | 12.3 |
| | | 203 | 131 | 11.2 | — | 17.5 | 12.3 |
| | Ave. | 197 | 132 | 10.8 | — | 17.7 | 11.9 |

Example 30

Proprocessability Study of Composite Fabrication

The ability to reprocess an ATT composite to correct flaws is considered an attractive feature. An LaRC-RP104 composite was purposely cured under 100 psi pressure resulting in a poorly consolidated composite material. The ultrasonic C-scan of this composite showed a considerable number of voids. This poor quality composite was then treated at 300° C. for ten minutes under 2500 psi pressure. This treatment yielded an improved composite the density of which increased from 1.41 g/cc to 1.55 g/cc. An ultrasonic C-scan also showed that the reprocessed composite was essentially void-free.

Example 31

RP83, LaRC-RP56, LaRC-RP57, LaRC-RP98, LaRC-RP99, LaRC-RP100 and LaRC-RP101. A typical procedure is described as follows: a resin solution was prepared by mixing 8.29 g of the Thermid AL-600 solution (National Starch, amic ester monomeric mixture having 75% solids in ethanol), 3.51 g of MA/MDA/6F and 20 ml of acetone. This resin solution was applied onto unsized AS-4 graphite fibers using a paint brush. A unidirectional composite was cured one hour at 250° C. under 200 psi pressure, followed by another hour at 288° C. under 500 psi pressure. The composite was then postcured at 288° C. for four hours. The composite fiber content varied in the range between 72 to 90 weight percent. Physical and mechanical properties of these miniature composites, which are presented in Tables 12 and 13, respectively, reflect the low resin content of the composites.

TABLE 12

COMPOSITE PHYSICAL PROPERTIES

| Composite | Fiber wt. % | Tg, °C. Dry | Tg, °C. Wet | Moisture uptake,[1] wt. % | Isothermal wt. loss,[2] % at 232° C. in air 500 hrs | Isothermal wt. loss,[2] % at 232° C. in air 1000 hrs | Temp., °C.,[3] at 5% wt. loss |
|---|---|---|---|---|---|---|---|
| AS-4/LaRC-RP80 | 81.5 | 282 | 258 | 0.6 | 0 | 0.3 | 540 |
| AS-4/LaRC-RP83 | 85.1 | 275 | 266 | 0.5 | 0 | 0.2 | 520 |
| AS-4/LaRC-RP57 | 85.9 | 312 | 280 | 0.8 | 0 | 0.2 | 560 |
| AS-4/LaRC-RP56 | 72.3 | 275 | 272 | 0.5 | 0 | 0.4 | 500 |
| AS-4/LaRC-RP98 | 89.9 | 287 | 285 | 1.9 | 0 | 0.1 | 536 |
| AS-4/LaRC-RP99 | 74.6 | 285 | 259 | 1.4 | 0.5 | 0.9 | 514 |
| AS-4/LaRC-RP101 | 78.5 | 310 | 289 | 0.5 | 0.2 | 0.6 | 585 |
| AS-4/LaRC-RP100 | 80.4 | 305 | 190 | 2.6 | 0.4 | 0.2 | 500 |

[1] Immersed in water for two weeks at room temperature
[2] In air circulating oven
[3] By TGA in air Preparation of Miniature Composites Because of the lack of experimental matrix materials, a miniature composite having dimensions of 8.89 cm by

TABLE 13

COMPOSITE MECHANICAL PROPERTIES

| | | Interlaminar shear strength, Ksi (% retention) | | | | |
|---|---|---|---|---|---|---|
| | | | 232° C. | | | |
| | | | | | Aged at 232° C. in air for | |
| Composite | Fiber wt. % | 25° C. | Dry | Wet | 500 Hrs. | 1000 Hrs. |
| AS-4/LaRC-RP80 | 81.5 | 8.7 | 4.8 | 5.5 (115) | 5.5 (115) | 5.9 (123) |
| AS-4/LaRC-RP83 | 85.1 | 8.5 | 4.5 | 5.4 (120) | 5.4 (120) | 4.7 (104) |
| AS-4/LaRC-RP57 | 85.9 | 8.7 | 4.1 | 4.3 (105) | 5.8 (142) | 6.4 (156) |
| AS-4/LaRC-RP56 | 72.3 | 13.4 | 5.5 | 5.9 (107) | 7.0 (127) | 9.2 (167) |

TABLE 13-continued

COMPOSITE MECHANICAL PROPERTIES

| | | Interlaminar shear strength, Ksi (% retention) | | | | |
|---|---|---|---|---|---|---|
| | | | | 232° C. | | |
| | | | | | Aged at 232° C. in air for | |
| Composite | Fiber wt. % | 25° C. | Dry | Wet | 500 Hrs. | 1000 Hrs. |
| AS-4/LaRC-RP98 | 89.9 | 9.0 | 6.2 | 6.2 (100) | — | 5.5 (189) |
| AS-4/LaRC-RP99 | 74.6 | 7.5 | 4.8 | 4.5 (94) | 4.5 (94) | 5.5 (115) |
| AS-4/LaRC-RP101 | 78.5 | 7.9 | 4.9 | 5.9 (121) | 5.5 (112) | 4.8 (98) |
| AS-4/LaRC-RP100 | 80.4 | 7.6 | 4.3 | 4.2 (98) | 3.3 (77) | 5.9 (137) |

Example 32

Synthesis of Biscitraconimides and Bismaleimides

Table 2 shows the chemical structures and designations of five biscitraconimides and five bismaleimides which were prepared for the ATT polymer synthesis described hereinabove. The following is a general synthetic procedure used for the preparation of the above ten compounds. The synthesis involves two steps. Step one concerns the preparation of the diamine from 4,4'-(hexafluoroisopropylidene)bis(o-phthalic anhydride), hereinafter referred to as 6F dianhydride, and the corresponding aromatic diamine. For example, 4,4'-[2,2,2-trifluoro-1-(trifluromethyl)ethylidene]bis(N-[α-(p-aminophenyl)-p-tolyl]phthalimide], hereinafter referred to as MDA/6F, was prepared by refluxing 4,4'-methylenedianiline (MDA) (0.48 mole) and 6F dianhydride (0.24 mole) in N-methyl-pyrrolidone (350 ml) for four hours. The cooled reaction mixture was poured onto an ice-water mixture (500 ml), and the solid was filtered, washed with distilled water (5×100 ml), and dried in vacuum at 100° C. to yield diamine MDA/6F in 99% yield. Using the same procedure given above, the following four diamines were also prepared: 4,4'-[2,2,2-trifluoro-1-(trifluoromethyl)ethylidene]bis[N-[p-(p-aminophenoxy)phenyl]phthalimide] (ODA/6F), 4,4'-[2,2,2-trifluoro-1-(trifluoromethyl)ethylidene]bis[N-)p-sulfanilylphenyl)phthalimide] (DDS/6F), 4,4'-[2,2,2-trifluoro-1-(trifluoromethyl)ethylidene]bis[N-(p-aminophenyl)phthalimide] (PD/6F) and 4,4'-[2,2,2-trifluoro-1-(trifluoromethyl)ethylidene]bis[N-(12-aminododecyl)phthalimide] (DDA/6F).

Step two is exemplified by the preparation of biscitraconimide CA/MDA/6F as described in the following Example 32(A):

32(A). To a refluxing and stirred solution of the diamine MDA/6F (0.05 mole) in 200 ml of a solvent mixture consisting of methylene chloride and acetone in 1:1 volume ratio, a solution of CA (0.1 mole) in 100 ml of the same solvent mixture was added over a 15 minute time period. After refluxing for ten minutes, the reaction solution changed color from dark brown to yellow and the solid material, identified to be the amic acid precursor, was precipitated. After one-half hour sodium acetate (5 g) and acetic anhydride (100 ml) were added to chemically imidize the amic acid into the corresponding imide. Immediately following the addition of acetic anhydride and sodium acetate, the reaction solution changed color from yellow back to dark brown and the solid material dissolved to give a clear brown solution. The progress of the reaction was followed by FTIR. After one hour the reaction product was worked up by washing three times with 200 ml saturated sodium carbonate aqueous solution, drying the organic materials with anhydrous magnesium sulfate and evaporating the organic solvents. This afforded the crude biscitraconimide CA/MDA/6F in 99% yield. After recrystallization from acetone/water, a pale yellow solid (overall yield 78%) was obtained, m.p. 190° C.-192° C.; IR (CHCl$_3$) 3100, 1775, 1720, 1635, 1375, 1260, 1140 and 1100 cm$^{-1}$. Analysis: Calcd. for C$_{55}$H$_{34}$N$_4$F$_6$O$_8$: C, 66.53; H, 3.43; N, 5.65, F, 11.49. Found: C, 64.48; H, 3.62; N, 5.51; F, 12.31.

32(B). As in Example 32(A), the reaction of CA (0.1 mole) and ODA/6F (0.05 mole) afforded the crude CA/ODA/6F in 99% yield, m.p. 138° C.-143° C. After recrystallization, a dark brown solid was obtained, m.p. 180° C.-182° C.; IR (CHCl$_3$) 3050, 1775, 1725, 1640, 1225, 1375, 1260, 1140 and 1100 cm$^{-1}$; $^1$H NMR: δ 2.09, 6.80, 7.20, 7.35, 7.91. Analysis: Calcd. for C$_{53}$H$_{30}$N$_4$F$_6$O$_{10}$: C, 63.86; H, 3.01; N, 5.62; F, 11.45. Found: C, 62.35; H, 3.29; N, 5.31; F, 13.26.

32(C). As in Example 32(A), the reaction of CA (0.1 mole) and DDS/6F (0.05 mole) afforded the crude CA/DDS/6F in 98% yield, m.p. 174° C.-180° C. After recrystallization, a gray solid was obtained, m.p. 210° C.-211° C.; IR (CHCl$_3$) 3030, 1770, 1720, 1350 and 1140 cm$^{-1}$. Analysis: Calcd. for C$_{53}$H$_{30}$N$_4$F$_6$O$_{12}$S$_2$: C, 58.24; H, 2.75; N, 5.13; F, 10.44; S, 5.86. Found: C, 57.39; H, 3.30; N, 4.73; F, 10.67; S, 5.98.

32(D). As in Example 32(A), the reaction of CA (0.1 mole) and PD/6F (0.05 mole) afforded the crude CA/PD/6F in 99% yield, m.p. 208° C.-212° C. After recrystallization, a dark purple solid was obtained, m.p. 230° C.-232° C.; IR (CHCl$_3$) 3030, 1760, 1715, 1640, 1375, 1260, 1140 and 1100 cm$^{-1}$. Analysis: Calcd. for C$_{41}$H$_{22}$N$_4$F$_6$O$_8$: C, 60.59; H, 2.71; N, 6.90; F, 14.04. Found: C, 60.32; H, 2.87; N, 6.75 F, 14.27.

32(E). As in Example 32(A), the reaction of CA (0.1 mole) and DDA/6F (0.05 mole) afforded the crude CA/DDA/6F in 99% yield, m.p. 121° C.-125° C. After recrystallization, a pale yellow solid was obtained, m.p. 132° C.-134° C.; IR (CHCl$_3$) 3300, 1760, 1720, 1375, 1260, 1140 and 1100 cm$^{-1}$. Analysis: Calcd. for C$_{43}$H$_{58}$N$_4$F$_6$O$_4$: C, 62.82; H, 7.35; N, 6.10; F, 11.89. Found: C, 63.86; H, 7.18; N, 6.93; F, 12.01.

32(F). As in Example 32(A), the reaction of maleic anhydride (MA) (0.1 mole) and MDA/6F (0.05 mole) afforded the crude MA/MDA/6F, m.p. 138° C.-143° C., in gold color.

32(G). As in Example 32(A), the reaction of MA (0.1 mole) and ODA/6F (0.05 mole) afforded the crude MA/ODA/6F, m.p. 130° C.-134° C. in dark brown color.

32(H). As in Example 32(A), the reaction of MA (0.1 mole) and DDS/6F (0.05 mole) afforded the crude MA/DDS/6F, m.p. 158° C.-163° C. in off-white color.

32(I). As in Example 32(A), the reaction of MA (0.1 mole) and PD/6F (0.05 mole) afforded the crude MA/PD/6F, m.p. 189° C.-193° C. in purple color.

32(J). As in Example 32(A), the reaction of MA (0.1 mole) and DDA/6F (0.05 mole) afforded the crude CA/DDA/6F in 89% yield, m.p. 105° C.–108° C. in light yellow color.

What is claimed is:

1. A process for the preparation of a tough, high performance polyimide, which process comprises reacting a triple bond conjugated with an aromatic ring in a bisethynyl compound with the active double bond in a compound containing a double bond activated toward the formation of a Diels-Alder type adduct which compound containing a double bond activated toward the formation of a Diels-Alder type adduct is a member selected from the group consisting of bismaleimides, biscitraconimides and benzoquinones.

2. The process of claim 1, which comprises the additional procedural step of addition curing the reaction product to produce a highly linear polymeric structure.

3. The process of claim 2, which comprises heat treating the highly linear polymeric structure to form a thermally-stable aromatic addition-type thermoplastic polyimide.

4. The process of claim 1, wherein the bisethynyl compound and the member selected from the group consisting of bismaleimides, biscitraconimides, and benzoquinones are reacted in stoichiometric quantities.

5. The process of claim 1, wherein the bisethynyl compound and the member selected from the group consisting of bismaleimides, biscitraconimides, and benzoquinones are reacted in off-stoichiometric quantities.

6. The process of claim 5, wherein the bisethynyl compound and the member selected from the group consisting of bismaleimides, biscitraconimides, and benzoquinones are present in a mole ratio between about 7:1 to 1:7.

7. A tough, high performance polyimide prepared by reacting a triple bond conjugated with an aromatic ring in a bisethynyl compound with the active double bond in a compound containing a double bond activated toward the formation of a Diels-Alder type adduct.

8. The polyimide according to claim 7, wherein the compound containing a double bond activated toward the formation of a Diels-Alder type adduct is a member selected from the group consisting of bismaleimides, biscitraconimides, and benzoquinones.

9. A tough, high performance, highly linear addition-type thermoplastic polyimide prepared by reacting a triple bond conjugated with an aromatic ring in a bisethynyl compound with the active double bond in a member selected from the group consisting of bismaleimides, biscitraconimides, and benzoquinones, followed by addition curing the reaction product.

10. A tough, thermally-stable, high performance, highly linear aromatic addition-type thermoplastic polyimide prepared by reacting a triple bond conjugated with an aromatic ring in a bisethynyl compound with the active double bond in a member selected from the group consisting of bismaleimides, biscitraconimides, and benzoquinones, followed by successive addition curing and heat treating the reaction product.

11. The polyimide of claim 8, wherein the bisethynyl compound and the member selected from the group consisting of bismaleimides, biscitraconimides, and benzoquinones are reacted in stoichiometric quantities.

12. The polyimide of claim 8, wherein the bisethynyl compound and the member selected from the group consisting of bismaleimides, biscitraconimides, and benzoquinones are reacted in off-stoichiometric quantities.

13. The polyimide of claim 12, wherein the bisethynyl compound and the member selected from the group consisting of bismaleimides, biscitraconimides, and benzoquinones are present in a mole ratio between about 7:1 and 1:7.

14. A molding compound comprising the polyimide of claim 7.

15. An adhesive composition comprising the polyimide of claim 7.

16. A polymer matrix composite comprising the polyimide of claim 7.

* * * * *